United States Patent [19]

Vidal et al.

[11] Patent Number: 4,903,390
[45] Date of Patent: Feb. 27, 1990

[54] SCALPEL BLADE REMOVER AND BLADE STORAGE APPARATUS

[75] Inventors: Claude Vidal, Santa Barbara; Al Plyley, Goleta; Vernon Vincent, Santa Barbara, all of Calif.

[73] Assignee: VIR Engineering, Inc., Goleta, Calif.

[21] Appl. No.: 251,759

[22] Filed: Oct. 3, 1988

[51] Int. Cl.⁴ .................. A61B 19/02; B23P 19/04
[52] U.S. Cl. .................................. 29/239; 29/278; 30/151; 206/355; 206/359
[58] Field of Search .................. 206/359, 355, 352; 29/278, 239; 30/151, 124, 339, 337

[56] References Cited

U.S. PATENT DOCUMENTS

| | | | |
|---|---|---|---|
| 2,782,787 | 2/1957 | Cary | 30/278 |
| 3,549,046 | 12/1970 | Iten | 206/355 |
| 4,168,777 | 9/1979 | Gaskell et al. | 206/359 |
| 4,395,807 | 8/1983 | Eldridge, Jr. et al. | 206/359 X |
| 4,466,539 | 8/1984 | Frauenhoffer | 206/359 |
| 4,730,376 | 3/1988 | Yamada | 206/359 X |
| 4,746,016 | 5/1988 | Pollak et al. | 206/359 |

Primary Examiner—Hien H. Phan
Assistant Examiner—Y. Lin
Attorney, Agent, or Firm—James E. Brunton

[57] ABSTRACT

A combination scalpel blade removal and storage apparatus having an easy to grip hourglass-shaped, disposable plastic housing which includes a strategically located safety shield that prevents accidental cuts during the blade insertion and removal process. The housing is provided with an internal, blade receiving channel which closely receives the blade and positively locates the tang portion of the handle within the housing. The blade stripping mechanism of the apparatus comprises an integrally formed, spring loaded lever arm disposed externally of the housing. Pressing the lever effortlessly deflects the heel of the blade away from the tang and over into a recessed stop, or pocket formed near the forward portion of the housing. Retraction of the handle with a straight line, continuous movement, while maintaining an inwardly directed force on the lever, smoothly strips the blade from the handle.

8 Claims, 3 Drawing Sheets

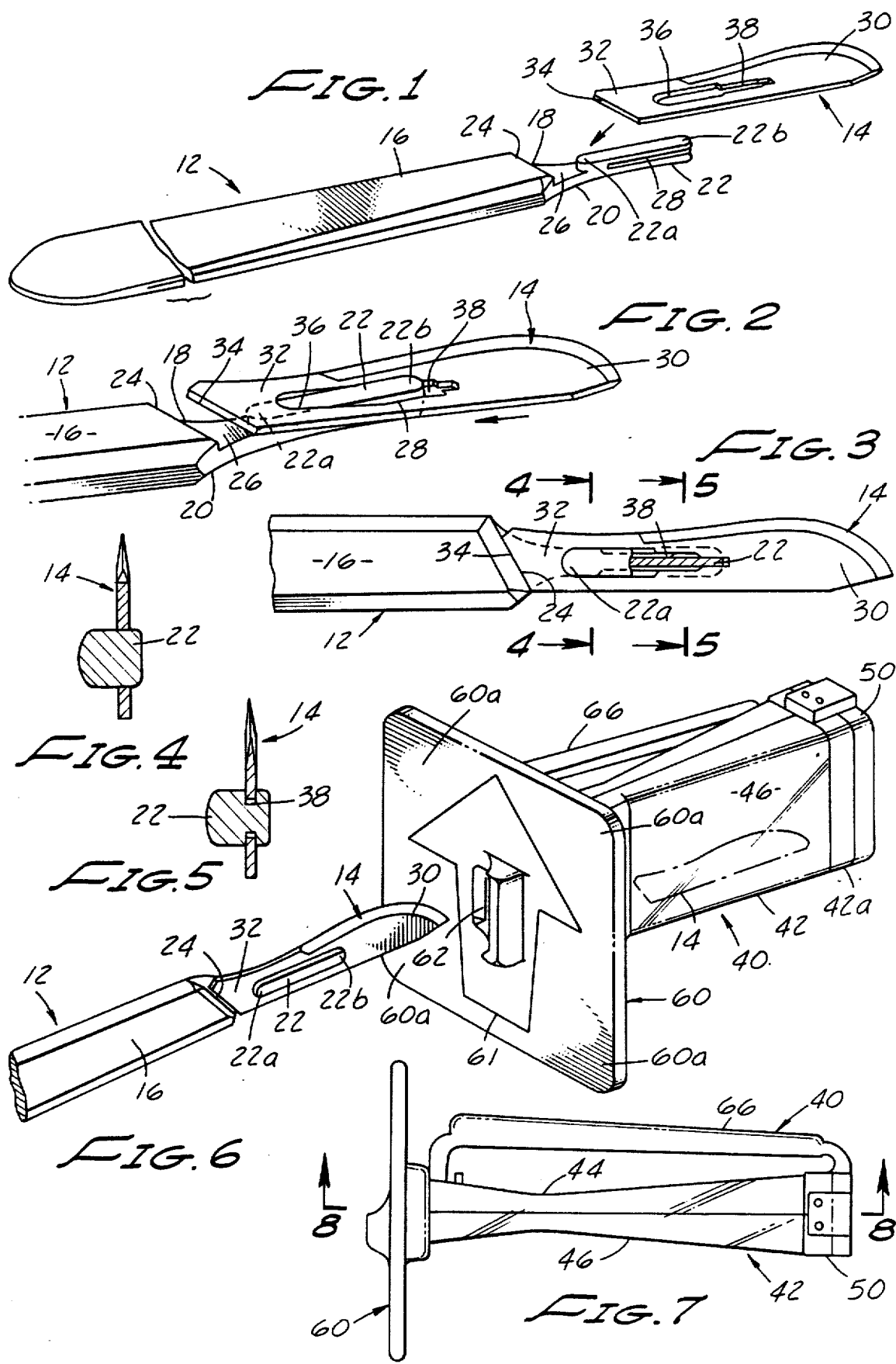

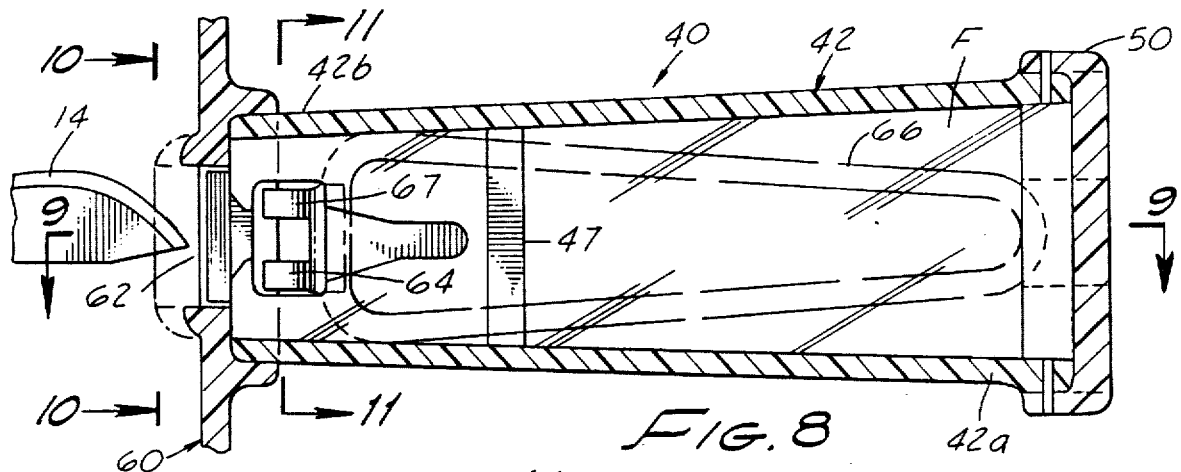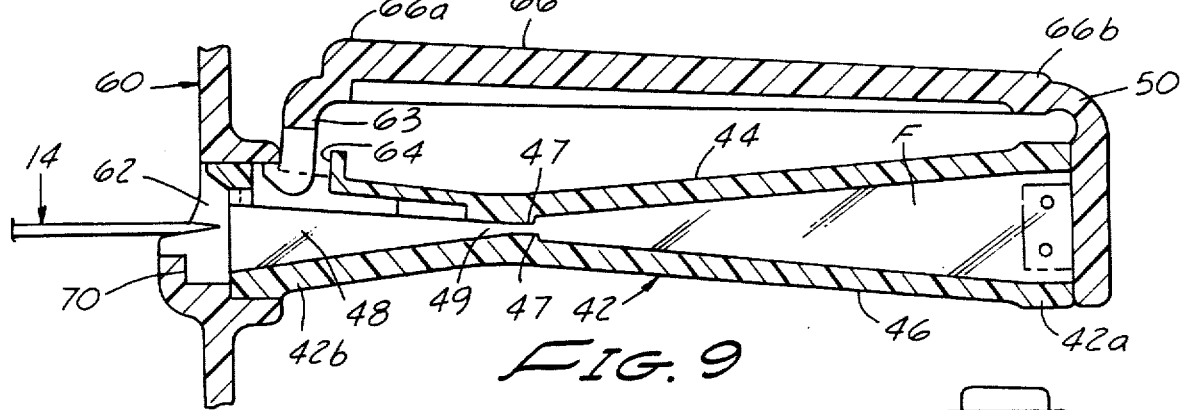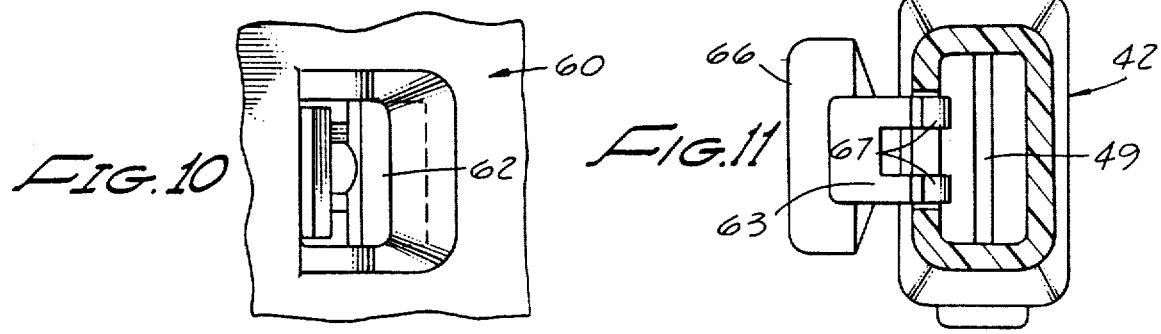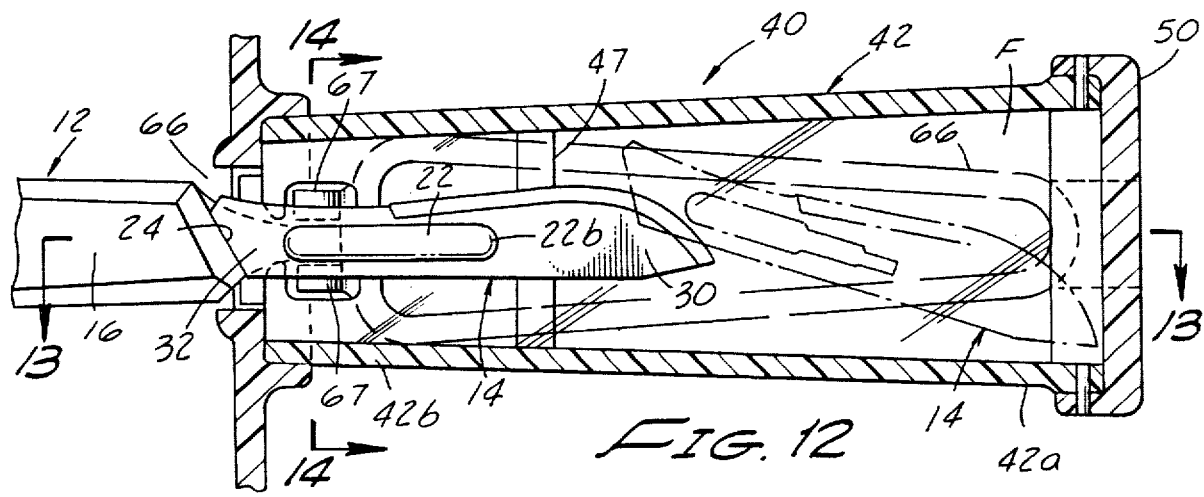

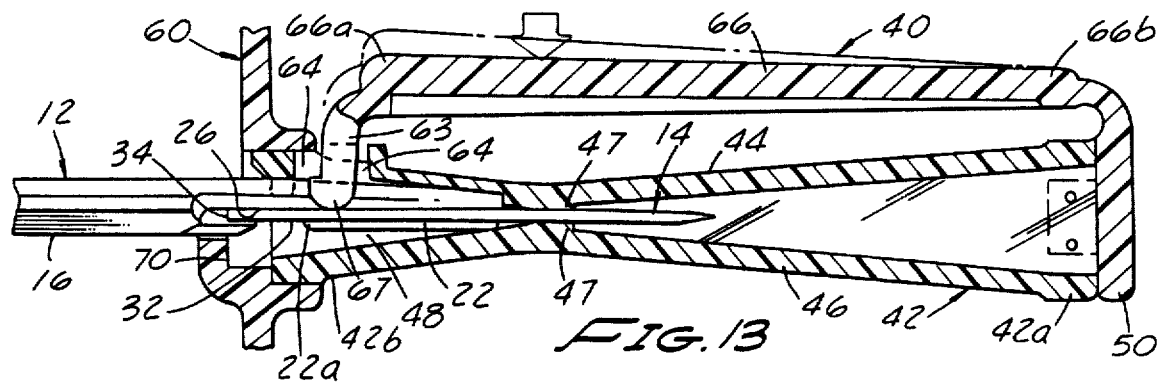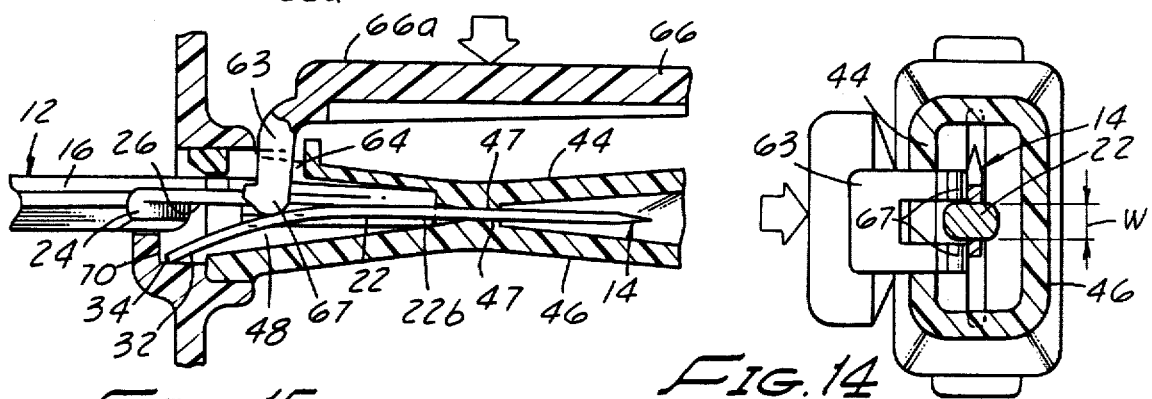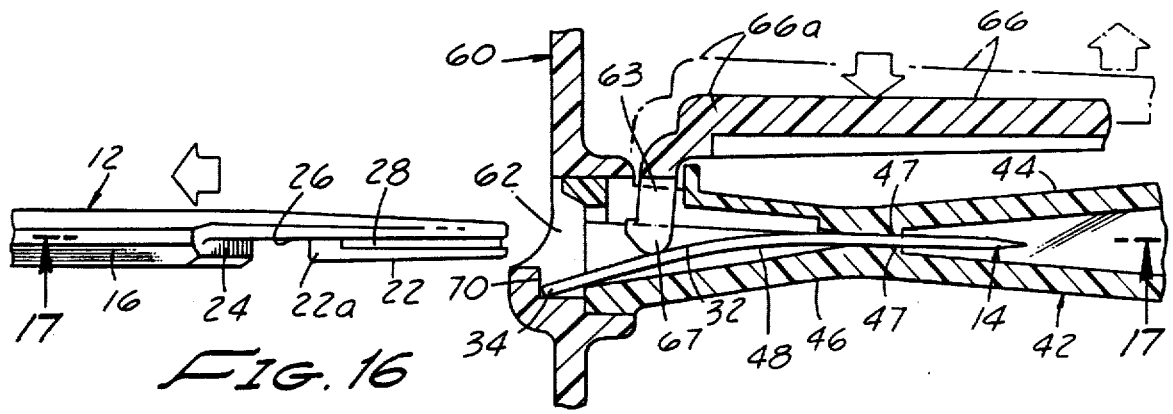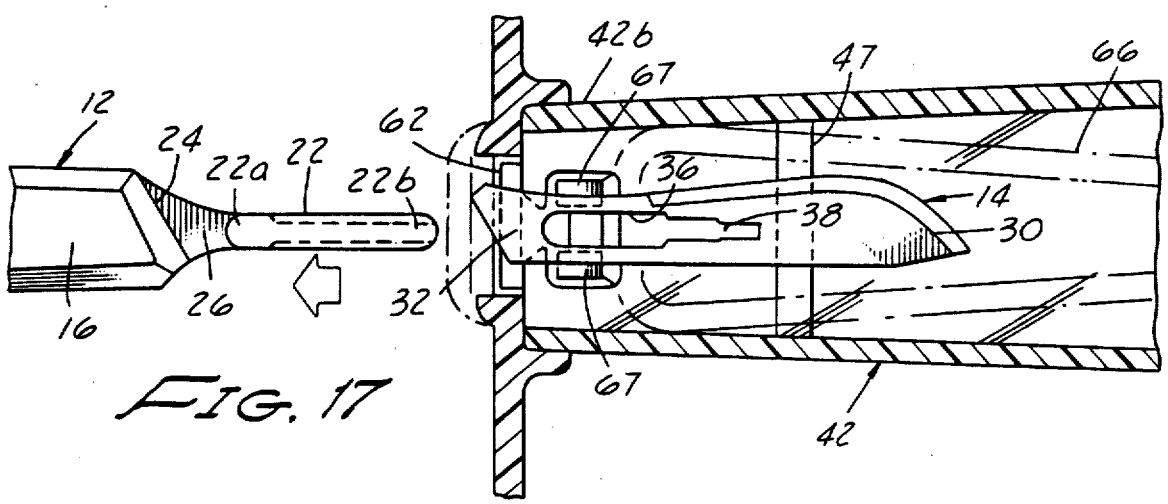

SCALPEL BLADE REMOVER AND BLADE STORAGE APPARATUS

BACKGROUND OF THE INVENTION

1. Field of the Invention

The present invention relates generally to a blade removal apparatus for removing a used blade from the handle of a surgical scalpel. More particularly the invention concerns a combination, spring loaded blade removing mechanism and safety shielded housing within which the blade drops for safe disposal.

2. Discussion of the Prior Art

Although the practice of medicine has progressed rapidly over the past century, the scalpel still remains the primary surgical tool. Operating rooms and emergency rooms in the U.S. alone use the scalpel over 50 million times each year. Many new products have been aimed at improving or replacing this tool; for example, disposable scalpels, electrocautery pencils and the like. However, the basic disposable blade attached to the reusable handle has continued to remain the standard.

Unfortunately, the risk of accidental cuts has been with the medical team as long as the scalpel. This risk is especially real to the operating or emergency room nurse who has to replace the "used" blade with a fresh one using either the fingers or a relatively clumsy forceps. The blade will frequently break and "fly" across the room, or much worse, the fingers will slip and the nurse suffers a nasty cut. Further, the onset of AIDS has justifiably expanded the medical team's concern over accidental cuts.

In accordance with standard practice, the prior art surgical scalpel includes a reusable, sterilizable handle having a tang on which the replaceable blade is mounted. The handle is typically subjected to repeatable uses. The blade, however, is always discarded at the end of a case, and, frequently, several blades are fitted on the same handle during the same procedure as they become dull or contaminated, or as a different style of blade is needed at different stages of the procedure. The interconnection between the blade and tang is usually such that the heel portion of the slotted blade must be deflected out of plane, that is away from the handle, when the blade is being assembled on, or disassembled from, the tang. The disassembly step can be difficult and dangerous, particularly when the scalpel is wet. After use, the blade is contaminated and is most hazardous to handle. Further, following complex surgery each blade must be accounted for. Accordingly a safe, systematic and reliable procedure must be adhered to during disassembly of the blade from the handle.

Several types and designs of devices have been proposed in the past in an effort to meet the stringent requirements for safe removal, accounting and disposal of used surgical blades, suturing needles and like articles. However, these devices have generally exhibited serious shortcomings. For example, the prior art devices are often quite complex, bulky and difficult to use. Many of the prior art surgical blade removal and storage units are extremely awkward to hold and manipulate and, therefore, themselves frequently contribute to injury during the blade removal step. Additionally, the blade storage portions of the devices are often poorly designed, so that the contaminated blades can accidentally fall from the device during transport. Finally, because of the complexity of the mechanism for deflecting the blade out of its plane in order to free it from the tang, many of the prior art devices are simply impractical to economically produce in the required quantities.

The apparatus of the present invention uniquely overcomes the drawbacks of the prior art blade removal and storage devices by providing a safety shielded apparatus having an easy to grip hourglass-shaped, disposable plastic housing which prevents accidental cuts during the blade insertion and removal process. The housing is provided with an internal, blade receiving channel which closely receives the blade and positively locates the tang portion of the handle within the housing. The blade stripping mechanism of the apparatus comprises an integrally formed, spring loaded lever arm disposed externally of the housing. Pressing the lever effortlessly deflects the heel of the blade away from the tang and over into a recessed stop, or pocket formed near the forward portion of the housing. Retraction of the handle with a straight line, continuous movement, while maintaining an inwardly directed force on the lever, smoothly strips the blade from the handle. The blade then falls by force of gravity through a narrow passageway into a storage compartment formed within the housing. In using the apparatus, no tilting or cumbersome manipulation of the scalpel is required. The user merely inserts the scalpel into an opening formed in the safety shield, presses the blade deflection lever and retracts the handle in a smooth straight line movement. The blade drops harmlessly into the clear plastic, hollow housing for later disposal. Integral ribs inside the plastic housing prevent accidental spillage of the contaminated blades for safety of handling and disposal.

SUMMARY OF THE INVENTION

It is an object of the present invention to provide a combination scalpel blade removal and storage apparatus which enables the removal of the used scalpel blade from a surgical scalpel in a completely safe manner.

It is another object of the invention to provide an apparatus of the aforementioned character which is compact, light weight and extremely easy to use.

Another object of the invention is to provide an apparatus as described in the preceding paragraphs which includes a closed compartment into which the the used blade drops upon being separated from the handle.

Still another object of the invention is to provide an apparatus of the class described which includes an hourglass shaped molded plastic housing to facilitate gripping and a spring loaded blade deflection lever integrally formed with the plastic housing for use in effortlessly stripping the used blade from the scalpel handle. A planar finger shield is mounted at the forward end of the housing to protect the user's fingers during insertion of the scalpel blade into the device.

Yet another object of the invention is to provide an apparatus of the class described which is of very simple construction and one which can be inexpensively manufactured in quantity.

Brief Description of the Drawings

FIG. 1 is a generally perspective view of a typical scalpel having a removable blade.

FIG. 2 is a fragmentary enlarged view illustrating the manner of mounting the scalpel blade on the handle.

FIG. 3 is a fragmentary plan view of a typical prior art scalpel shown partly in cross-section to illustrate the interconnection of the blade with the handle.

FIG. 4 is a cross-sectional view taken along Lines 4—4 of FIG. 3.

FIG. 5 is a cross-sectional view taken along Lines 5—5 of FIG. 3.

FIG. 6 is a generally perspective view of the blade removal and containing apparatus of the present invention showing a scalpel handle and connected blade in position for insertion into the device of the invention.

FIG. 7 is a top view of the blade removal and container apparatus of the invention.

FIG. 8 is a cross-sectional view taken along Lines 8—8 of FIG. 7.

FIG. 9 is a cross-sectional view taken along Lines 9—9 of FIG. 8.

FIG. 10 is a fragmentary view taken along Lines 10—10 of FIG. 8 showing the blade insertion opening in the planar shield of the apparatus of the invention.

FIG. 11 is a cross-sectional view taken along Lines 11—11 of FIG. 8 illustrating the appearance of the blade deflecting arm of the apparatus in an at-rest configuration.

FIG. 12 is a fragmentary side-elevational, cross-sectional view of the apparatus of the invention showing the scalpel blade positioned internally of the apparatus. The phantom lines in FIG. 12 illustrate the scalpel blade after its removal from the handle portion of the scalpel.

FIG. 13 is a cross-sectional view taken along Lines 13—13 of FIG. 12.

FIG. 14 is a cross-sectional view taken along Lines 14—14 of FIG. 12.

FIG. 15 is a fragmentary cross-sectional view similar to FIG. 13, but showing the blade deflecting arm of the apparatus acting upon the heel portion of the scalpel blade to permit removal of the used blade from the handle.

FIG. 16 is a fragmentary cross-sectional view similar to FIG. 13, but illustrating the appearance of the apparatus of the invention after the blade has been removed from the handle and the handle withdrawn from the opening in the apparatus.

FIG. 17 is a view taken along Lines 17—17 of FIG. 16, illustrating the used scalpel blade being held captive within the blade container of the apparatus by the blade deflecting arm.

DESCRIPTION OF THE INVENTION

Referring to the drawings, and particularly FIGS. 1 through 5, the construction of a typical surgical scalpel is there illustrated. The surgical scalpel generally includes an elongated handle portion 12 and a removable blade portion 14. Handle 12 is usually provided with a forward body section 16 which gradually narrows in width by means of concavely curved sides 18 and 20 into a forwardly extending tang 22. The upper side of the handle section 16 is provided with an angled surface 24 (FIG. 3) which slopes downwardly forming a recess 26 between the forward body portion 16 and an upwardly projecting portion 22a of tang 22. The forwardmost portion 22b of tang 22 is typically provided with a longitudinally extending groove 28 which extends on each side of the tang 22 from its front edge rearwardly about three-quarters of the length of the tang.

Blade 14 typically includes a forward cutting section 30 and a rearward heel portion 32. Heel portion 32 terminates in a back edge 34 which is angled to abut the angled surface 24 of the handle 12. Blade 14 also generally has a first opening or aperture 36 which communicates with a narrow second, slot like aperture 38.

In order to mount blade 14 on handle 12, the edges of second aperture 38 are inserted into grooves 28 in the manner shown in FIG. 2. The blade is then slid rearwardly within grooves 28 toward handle portion 16. During this sliding process the blade 14 is somewhat distorted from its planar configuration. As end portion 22a of tang 22 begins to fit within first opening 36, the heel portion of the blade reaches a position where it snaps over the tang 22 (FIG. 3). In this way blade 14 is locked onto the handle 12 because, as indicated in FIGS. 3 and 4, aperture 38 is narrower than the width of the tang 22. When the blade 14 is thus mounted on the handle, the back edge 34 of the blade abuts the angle surface 24 of the handle 12, holding the blade securely in position. As shown in FIG. 3, the angle of back edge 34 and the angled surface 24 requires that when the blade is correctly mounted on the handle, the cutting portion will always be directed upwardly in the manner indicated in FIG. 3.

In order to remove the blade 14 from the handle 12, the heel portion 32 of the blade must be forced out of plane and away from portion 26 of the handle until it disengages from end 22a of tang 22. The blade and handle are then moved relative to one another until tang 22 is removed from aperture 38. This frees the blade 14. As previously mentioned, when this blade removal procedure is attempted by hand, a serious cut can easily occur.

Turning now to FIG. 6 through 9, the apparatus of the present invention for safely removing the blade from the handle is there shown and generally designated by the numeral 40. In the embodiment of the invention shown in the drawings, the apparatus comprises a hollow housing 42 having first and second ends 42a and 42b and inwardly converging side walls 44 and 46. As best seen by referring to FIG. 9, the forward portions of walls 44 and 46 cooperate to define an inwardly tapering receiving channel 48. It is to be observed that the walls converge inwardly from both the forward and rearward ends of the housing to form a narrow passageway 49 adapted to closely receive and locate the forward portion of the scalpel handle and the scalpel blade. . This unique feature of the apparatus of the invention, which will be discussed in greater detail hereinafter, properly locates the scalpel and prevents transverse movement of the blade and handle during removal of the used scalpel blade.

Hollow housing 42 is preferably molded from a suitable moldable plastic material such as polypropylene, or the like, in a manner such that first end 42a is closed by a closure 50. Second end 42b of the housing remains open after molding as indicated in FIG. 8. Mounted at the open end 42b of the housing is the important shield means and blade stop means the invention now to be described.

The shield means of the present form of the invention, which is connected to the housing 42 proximate the second 42b thereof, performs the important function of shielding the fingers of the user of the apparatus while gripping the hourglass shaped housing during the blade removal operation. The shield means here comprises a generally rectangular shielding member 60 having a centrally located receiving slot 62 formed therethrough. Finger shielding portions 60a of the shield means extend outwardly from slot 62 in the manner shown in FIG. 6.

Also forming an important feature of the present form of the invention is a blade stop means formed on member 60 and disposed proximate slot 62 for engaging the heel of the scalpel blade to block removal of the blade from the blade receiving channel 48 during removal of the used blade from the handle. The particulars of construction of the stop means, and its function, will be described in greater detail in the paragraphs which follow.

Forming still another important aspect of the apparatus of the present invention is blade deflecting means for controllably deflecting the heel of the scalpel blade out of plane when the blade is correctly located within the blade receiving channel 48 of housing 42. The blade deflections means functions to pressurally engage the heel of the scalpel blade and urge its movement into a location wherein the edge 34 of the heel of the scalpel blade engages the stop means to block removal of the blade from the blade receiving channel 48. In the embodiment of the invention shown in the drawings, the blade deflecting means comprises a specially configured blade deflecting arm 63 which extends through an opening 64 provided in side wall 44 (FIG. 9). Integrally formed with arm 63, is a generally perpendicularly disposed actuating arm 66 located exteriorly of housing 42. The first end 66a of actuating arm 66, is preferably integrally the with arm 63. The second end 66b of actuating arm 66 is also desirably integrally formed with end wall 50. The blade deflecting means is preferably formed of a yieldable plastic material so that the juncture between the actuating arm 66 and the closure wall 50 forms a living hinge.

As best seen by referring to FIG. 10 and 14, blade deflecting arm 63 is provided at its free end with a pair of blade engaging elements 67 which are spaced apart a distance slight greater than the width "W" of the tang 22. As illustrated in FIG. 15, with the scalpel blade disposed within channel 48, the blade engaging elements 67 can pressurally engage the heel 32 of the scalpel blade in a manner such that an inward pressure exerted on the actuating arm 66 will deflect the heel portion of the scalpel blade out of its plane and away from handle portion 16.

Referring again to FIG. 9, it is important to note that, when the blade deflecting means of the apparatus is in the at-rest position shown in FIG. 9, elements 67 of are 63 are disposed in a first location well outside blade receiving channel 48 so as not to interfere with insertion of blade 14 into housing 42 in the manner illustrated in FIG. 9. An arrow 61 is imprinted on planar shield 60a to indicate that the scalpel is to be inserted with the cutting edge of the blade extending upwardly. Once the scalpel blade is inserted into channel 48 in the manner shown in FIG. 13, a force exerted on actuating arm 66 will cause the living hinge to flex so that elements 67 of arm 63 will move into a second position in engagement with the heel portion of the scalpel blade. A continued exertion of force on actuating arm 66 in the direction of the arrow of FIG. 15 will move elements 67 to a third position causing deflection of the heel 32 of the scalpel blade out of plane to a position where edge 34 of the blade moves into close proximity with wall 70 of the stop means.

A smooth straight line withdrawal of the scalpel handle as illustrated in FIG. 17 will cleanly strip the blade from the tang. As indicated by the phantom lines in FIG. 12, the blade 14 will then fall into the forward portion "F" of the closed housing. As best seen in FIG. 9 the walls 44 and 46 of the housing are provided with inwardly extending steps 47 which are disposed slightly forwardly of passageway 49. These steps function to prevent accidental movement of the used blade through passageway 49 and into the forward portion of the housing where the used blade might escape from the housing through receiving slot 62.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A combination scalpel blade removal and used blade storage apparatus for use in connection with a changeable blade scalpel of the character having a blade with a cutting portion and heel portion removably mounted on a handle by fitting a mounting aperture formed in the heel portion of the blade over a grooved blade mounting tang provided on the handle, said apparatus comprising:
   (a) a hollow housing having first and second ends and spaced apart, inwardly converging side walls defining a receiving channel for receiving the scalpel blade and a portion of the scalpel handle, one of said side walls having an opening therein located proximate said second end of said housing, said side walls converging to define a restricted opening;
   (b) shield means connected to said housing proximate said second end thereof for shielding the fingers of a user of the apparatus while gripping said housing, said shield means comprising a shielding member having a receiving slot in communication with said receiving channel and, finger shielding portions extending outwardly from said spaced apart side walls a sufficient distance to shield those fingers of the user of the apparatus in gripping engagement with said side walls;
   (c) blade deflecting means mounting on said hollow housing for engaging the blade to deflect the heel of the blade away from the scalpel handle, when the blade is within said receiving channel, said blade deflecting means comprising a blade deflecting arm extending through said opening formed in said one of said side walls, said blade deflecting arm having a blade engaging portion movable sequentially from a first position located outside said blade receiving channel to a second position in pressural engagement with the heel of the blade to a third position wherein the heel portion of the blade is deflected away from the scalpel handle; and
   (d) stop means mounted on said hollow housing proximate said receiving slot for engaging the heel of the blade when said blade engaging portion of said blade deflecting arm is in said third position for blocking removal of the blade from said receiving channel.

2. An apparatus as defined in claim 1 in which said blade deflecting means further includes an actuating arm disposed exteriorly of said housing and having first and second ends, said first end being connected to said blade deflecting arm and said second end being connected to said housing proximate said first end thereof.

3. An apparatus as defined in claim 1 in which said blade engaging portion of said blade deflecting arm comprises a pair of blade engaging elements spaced apart a distance slightly greater than the width of the tang on the handle of said scalpel.

4. An apparatus as defined in claim 1 further including cover means for closing said first end of said hollow housing to form a used blade receiving compartment.

5. An apparatus as defined in claim 4 in which one of said side walls of said housing is provided with locating means for locating the portion of the scalpel handle within said receiving channel.

6. A combination scalpel blade removal and used blade storage apparatus for use in connection with a changeable blade scalpel of the character having a blade with a cutting portion and heel portion removably mounted on a handle by fitting a mounting aperture formed in the heel portion of the blade over a grooved blade mounting tang provided on the handle, said apparatus comprising:

(a) a hollow housing having first and second ends, said housing being closed at said first end and interconnected top, bottom and side walls defining a receiving channel for receiving the scalpel blade and a portion of the scalpel handle, said side walls converging inwardly from both said first and second ends of said housing to form a restricted opening having a width slightly greater than the thickness of the blade, one of said walls having an opening therein located proximate said second end of said housing;

(b) shield means connected to said housing proximate said second end thereof for shielding the fingers of a user of the apparatus while gripping said housing, said shield means comprising a generally planar shaped shielding member having a receiving slot in communication with said receiving channel and, finger shielding portions extending outwardly a substantial distance from said side walls;

(c) blade deflecting means mounted on said hollow housing for engaging the blade to deflect the heel of the blade away from the scalpel handle, when the blade is within said receiving channel, said blade deflecting means comprising an actuating arm having first and second ends, said first end being connected to said housing and a blade deflecting arm extending through said opening formed in said wall, said blade deflecting arm being connected with said second end of said actuating arm and having a blade engaging portion comprising a pair of blade engaging slots spaced apart a distance slightly greater than the width of the blade mounting tang and being movable sequentially from a first position located outside said blade receiving channel to a second position in pressural engagement with the heel of the blade to a third position wherein the heel portion of the blade is deflected away from the scalpel handle; and (d) stop means mounted on said shielding member proximate said receiving slot for engaging the heel of the blade when said blade engaging portion of said blade deflecting arm is in said third position for blocking removal of the blade from said receiving channel.

7. An apparatus as defined in claim 6 in which each of said side walls of said housing is provided with a step portion located proximate the convergence of said side walls for restricting movement of said used blade toward said receiving slot following removal of the blade from the scalpel handle.

8. An apparatus as defined in claim 7 in which one of said side walls of said housing is provided with locating means for locating the portion of the scalpel handle within said receiving channel.

* * * * *